United States Patent
Ohama

(10) Patent No.: US 8,835,876 B2
(45) Date of Patent: Sep. 16, 2014

(54) INSPECTION APPARATUS FOR SHEET

(71) Applicant: Komori Corporation, Tokyo (JP)

(72) Inventor: Kentaro Ohama, Tsukuba (JP)

(73) Assignee: Komori Corporation, Tokyo (JP)

( * ) Notice: Subject to any disclaimer, the term of this patent is extended or adjusted under 35 U.S.C. 154(b) by 0 days.

(21) Appl. No.: 14/030,587

(22) Filed: Sep. 18, 2013

(65) Prior Publication Data

US 2014/0077101 A1    Mar. 20, 2014

(30) Foreign Application Priority Data

Sep. 19, 2012   (JP) ................................. 2012-205373

(51) Int. Cl.
| | | |
|---|---|---|
| *G01N 21/64* | (2006.01) | |
| *G07D 7/12* | (2006.01) | |
| *G01N 21/89* | (2006.01) | |
| *B41F 33/00* | (2006.01) | |

(52) U.S. Cl.
CPC .............. *G01N 21/6456* (2013.01); *G07D 7/12* (2013.01); *G01N 21/89* (2013.01); *B41F 33/0036* (2013.01)
USPC ..................................................... 250/461.1

(58) Field of Classification Search
CPC .. G01N 21/643; G01N 21/86; G01N 21/6456
USPC ....................................................... 250/461.1
See application file for complete search history.

(56) References Cited

U.S. PATENT DOCUMENTS

| | | | | |
|---|---|---|---|---|
| 5,825,945 A | * | 10/1998 | Stolis et al. ................... | 382/312 |
| 2002/0079454 A1 | * | 6/2002 | Yamada et al. ............ | 250/358.1 |

FOREIGN PATENT DOCUMENTS

JP         2010-221410 A      10/2010

* cited by examiner

*Primary Examiner* — Marcus Taningco
(74) *Attorney, Agent, or Firm* — Birch, Stewart, Kolasch & Birch, LLP

(57) ABSTRACT

An inspection apparatus for a sheet of paper subjected to a process to impart a translucent property such as a "watermark" or a "security window" includes: an inspection cylinder in which a surface facing the sheet of paper is provided with a luminescence-producing portion; UV-LED illuminators which irradiate the sheet of paper with light containing the ultraviolet rays; a color camera which images the sheet of paper; an ultraviolet cut filter which eliminates the ultraviolet rays in the light emitted from the UV-LED illuminators and reflected off the sheet of paper as well as the luminescence-producing portion and makes only the light having wavelengths longer than wavelengths of the ultraviolet rays incident on the color camera; and a control device which determines appropriateness of a processed portion on the sheet of paper having the translucent property on the basis of luminescence in a visible light range produced by the luminescence-producing portion and made incident on the color camera.

1 Claim, 3 Drawing Sheets

INSPECTION APPARATUS FOR SHEET

TECHNICAL FIELD

The present invention relates to an inspection apparatus for a sheet subjected to a process to impart a translucent property such as a "watermark" or a "security window".

BACKGROUND ART

In order to prevent counterfeiting, printing products such as bank notes and securities are often subjected to a process to impart a translucent property such as a "watermark" or a "security window" onto a sheet surface or to the inside of the sheet apart from ordinary pattern portions. The "watermark" is a distinguishable image or marking that appears more brightly on paper upon its irradiation with light (or more darkly with light reflected against a dark background). A typical watermark is textured in its manufacturing process by partially changing the thicknesses of the paper with a water-coated metal stamp or the like to form an embossed portion and a recessed portion on the paper. Another special watermark used in bank notes and the like is called a shaded watermark. In contrast to the typical watermark, the shaded watermark employs a technique to increase the thickness of a portion corresponding to an image or marking. In this way, the shaded watermark can express gradation of shades and thus achieve picturesque expression. Meanwhile, the "security window" means a transparent region consisting of a film of a transparent polymer sheet without base printing on both sides. A portrait or characters may further be printed in the security window.

Accordingly, printing products subjected to the process to impart a "watermark" or a "security window" need to be inspected for their presence and absence as well as their contours and locations.

CITATION LIST

Patent Literature

{Patent Literature 1} Japanese Patent Application Publication No. 2010-221410

SUMMARY OF INVENTION

Technical Problem

Although various inspection apparatuses including the one in Patent Literature 1 have heretofore been proposed as inspection apparatuses for pattern portions printed with an ordinary ink, there have been no measures to inspect a printing product subjected to a process to impart a translucent property such as a "watermark" or a "security window" for its presence and absence as well as its contour and location.

The present invention has been made to solve the aforementioned problem. An object of the present invention is to provide an inspection apparatus for a sheet, which is capable of conducting detailed inspection of a printing product subjected to a process to impart a translucent property such as a "watermark" or a "security window" for the presence, contour, and location thereof.

Solution to Problem

The inspection apparatus for a sheet of the present invention for solving the foregoing problem is an inspection apparatus for a sheet subjected to a process to impart a translucent property, characterized in that the inspection apparatus includes: a support member in which a surface facing the sheet is processed with a material to produce luminescence in a visible light range upon irradiation of ultraviolet rays; a light source configured to irradiate the sheet with light containing the ultraviolet rays; imaging means for imaging the sheet; an ultraviolet filter configured to eliminate the ultraviolet rays in the light emitted from the light source and reflected off the sheet and the support member, and to make only the light having wavelengths longer than wavelengths of the ultraviolet rays incident on the imaging means; and a control device configured to determine appropriateness of the process to impart a translucent property performed on the sheet on the basis of the luminescence in the visible light range produced by the support member and made incident on the imaging means.

Advantageous Effects of Invention

According to the inspection apparatus for a sheet of the present invention, the ultraviolet rays emitted from the light source penetrates only the processed portion having the translucent property such as a "watermark" or a "security window" and irradiates the support member, whereby the processed portion produces luminescence at the time of imaging it by the imaging means whereas the remaining portion becomes dark. Thus, it is possible to conduct detailed inspection of the processed portion having the translucent property such as the "watermark" or the "security window" for the presence, contour, and location thereof.

DESCRIPTION OF EMBODIMENT

An inspection apparatus for a sheet according to the present invention will be described below in detail with reference to the drawings.

{Embodiment}

Figure 1:
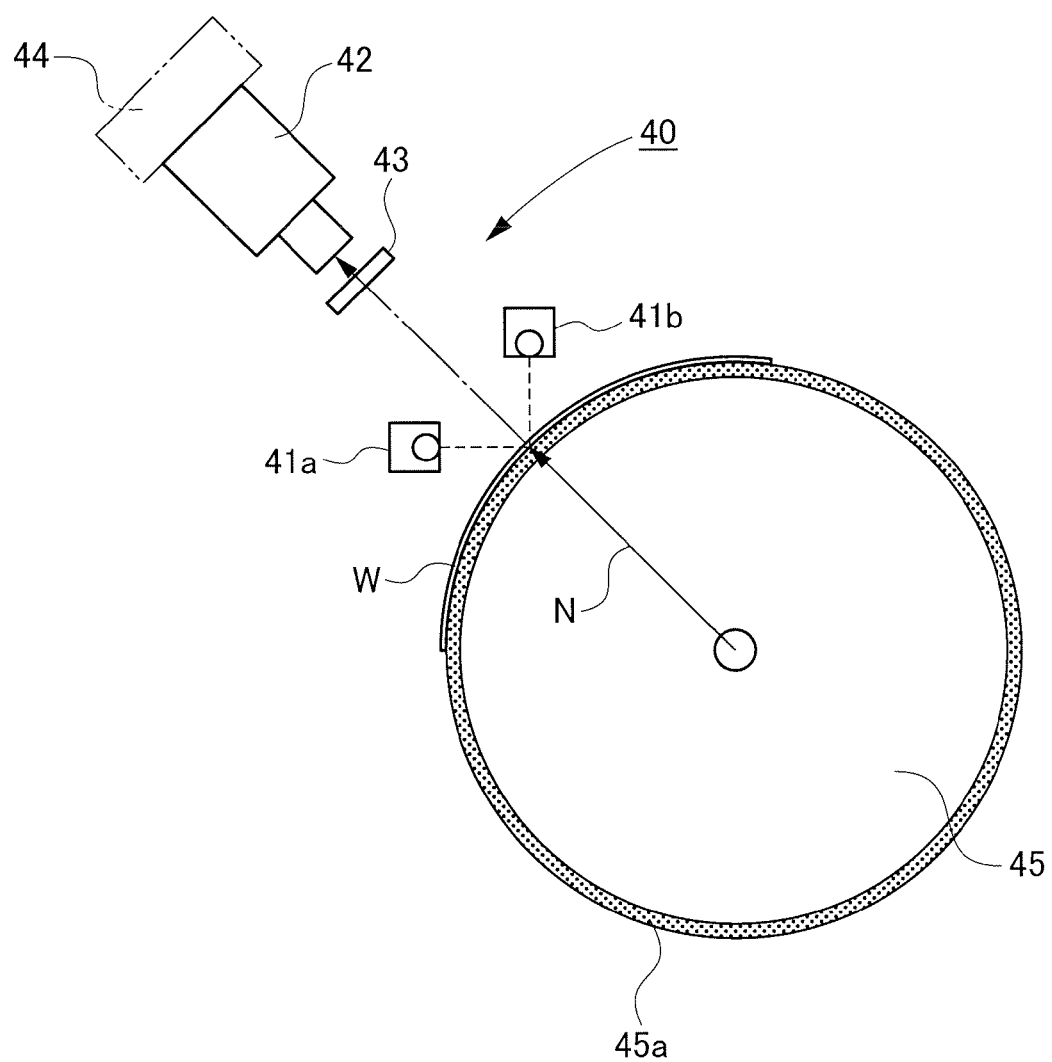
FIG. 1 is a schematic configuration diagram of an inspection apparatus according to an embodiment of the present invention.
Figure 2:
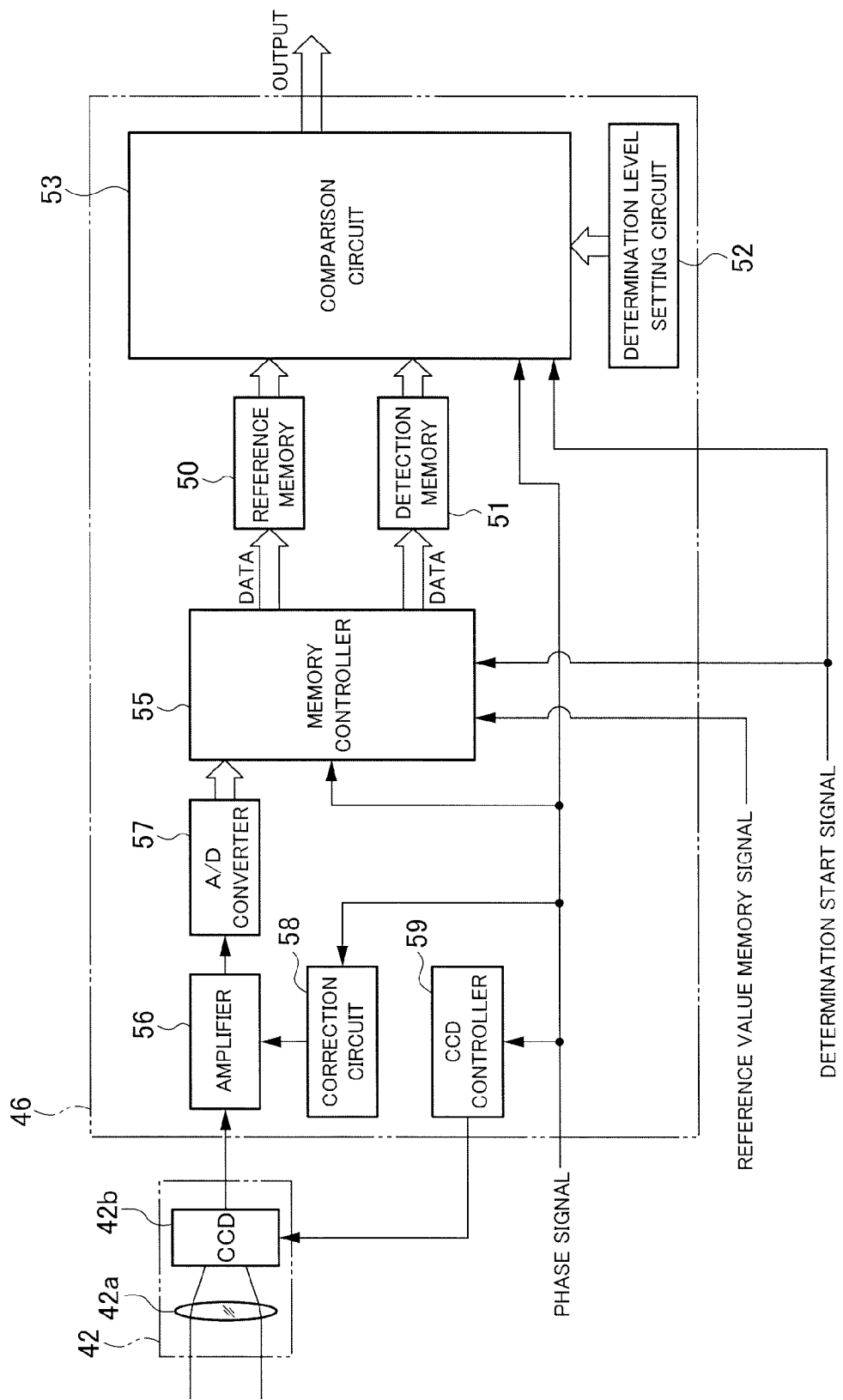
FIG. 2 is a control block diagram according to the embodiment of the present invention.
Figure 3:
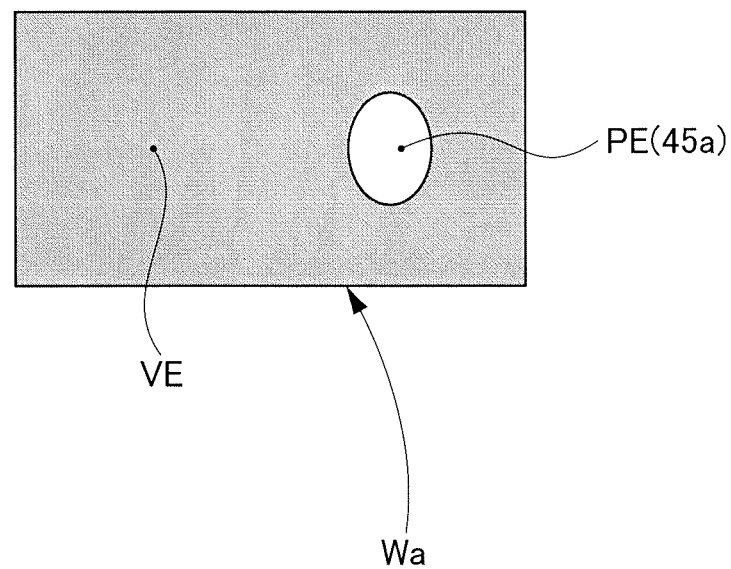
FIG. 3 is an explanatory view of a pattern portion on a piece of paper.

FIG. 1 is a schematic configuration diagram of an inspection apparatus according to an embodiment of the present invention, and FIG. 2 is a control block diagram thereof. Meanwhile, FIG. 3 is an explanatory view of a pattern portion on a piece of paper.

As shown in FIG. 1, a sheet of paper (a sheet) W subjected to a process to impart a translucent property such as a "watermark" or a "security window" by a not-shown processing machine is delivered to an inspection cylinder (a support member; note that an impression cylinder or a transfer cylinder may replace the inspection cylinder) 45. A surface of the inspection cylinder 45 is provided with a luminescence-producing portion 45a in a predetermined thickness, which is processed with a material that produces luminescence upon its irradiation with ultraviolet rays. The luminescence-producing portion 45a may preferably be formed by coating a peripheral surface of the inspection cylinder 45 with a fluorescent paint or by wrapping a film containing either a fluorescent dye or a fluorescent paint around the inspection cylinder 45, for example.

Then, the sheet of paper W inspected for its printing quality by means of an inspection apparatus 40 provided facing the peripheral surface of the inspection cylinder 45 is sent to a sheet delivery unit via not-shown conveying means, and is then stacked on a delivery pile board (a pile).

The inspection apparatus 40 is configured to inspect a processed portion of the sheet of paper W where a translucent property such as a "watermark" or a "security window" is imparted. The inspection apparatus 40 includes: a pair (or any other number) of UV(ultraviolet)-LED illuminators (such as light sources with a peak wavelength at 365 nm) 41a and 41b configured to irradiate the sheet of paper W with light including ultraviolet rays; one color camera (imaging means) 42 configured to image the sheet of paper W; an ultraviolet cut filter (an ultraviolet filter) 43 configured to eliminate light components having wavelengths in a UV range, equal to or shorter than 410 nm, from the light emitted from the UV-LED illuminators 41a and 41b and reflected off the sheet of paper W as well as the inspection cylinder 45, and to make only light components having wavelengths longer than wavelengths of the ultraviolet rays incident on the color camera 42; and a control device 46 configured to determine appropriateness of a processed portion of the sheet of paper W having a translucent property such as a "watermark" or a "security window" on the basis of the light components in a visible light range having the wavelengths longer than the wavelengths of the ultraviolet rays, the light components being produced by the luminescence-producing portion 45a of the inspection cylinder 45 and made incident on the color camera 42.

The color camera 42 is provided in a direction of a normal N to the center line (the cylinder axis) of the inspection cylinder 45, and is supported by a not-shown apparatus frame via a support frame 44 in a position at which to image an imaging plane of the sheet of paper W in a perpendicular direction. The UV-LED illuminators 41a and 41b are also supported by the apparatus frame via not-shown support frames. Here, the inspection apparatus 40 may be installed in a darkroom that is provided separately from the printing press.

Next, an optical and electrical configuration of the inspection apparatus 40 of the embodiment will be described with reference to FIG. 2. As described above, the inspection apparatus 40 includes the color camera 42 configured to image the sheet of paper W, and the control device 46 configured to inspect the processed portion of the sheet of paper W having the translucent property on the basis of an imaging output from the color camera 42. The color camera 42 includes an optical system having a lens 42a, and a CCD (charge coupled device) 42b configured to convert an image formed by the optical system into an electric signal.

The control device 46 includes: a reference memory 50 configured to store a reference image signal; a detection memory 51 configured to store a detection image signal; a memory controller 55 configured to control writing and reading of the signals in and out of the reference memory 50 and the detection memory 51; a determination level setting circuit 52 configured to set an allowable level difference between a pair of signals read out of the reference memory 50 and the detection memory 51; a comparison circuit 53 configured to compare the pair of signals in consideration of the allowable level difference set by the determination level setting circuit 52; an amplifier 56 configured to amplify an output from the CCD 42b; an A/D converter 57 configured to perform analog-to-digital conversion of an output from the amplifier 56 and to output the converted output to the memory controller 55; a correction circuit 58 configured to adjust gains of the amplifier 56; and a CCD controller 59 configured to control the CCD 42b.

At the start of a printing job, the reference memory 50 stores reference image data which are read out of the processed portion having the translucent property, which is processed normally on the sheet of paper W. Here, the reference memory 50 stores different image data for each printing job. The detection memory 51 stores detection image data read out of the sheet of paper W as an object of inspection.

The memory controller 55 controls writing and reading of the data in and out of the reference memory 50 and the detection memory 51. The determination level setting circuit 52 presets the allowable level difference between the reference image data read out of the reference memory 50 and the detection image data read out of the detection memory 51.

If the level difference between the reference image data and the detection image data read by the memory controller 55 is equal to or above the allowable level difference set by the determination level setting circuit 52, the comparison circuit 53 outputs a signal indicating that the quality of the Processed portion having the translucent property is defective. Specifically, pieces of the reference image data and pieces of the detection image data corresponding to pixels of the CCD 42b are compared on a one-for-one basis, whereby the levels of the two types of data corresponding to the respective pixels are compared. A defective signal is outputted if any one of the level differences is equal to or above the allowable level difference.

To be more precise, the comparison circuit 53 performs a first comparison operation to sequentially compare the pieces of the reference image data read out of the reference memory 50 with the pieces of the detection image data read out of the detection memory 51 on the pixel basis. Next, the comparison circuit 53 performs a second comparison operation to compare the level differences between the pairs of signals obtained by the first comparison operation with the allowable level difference outputted from the determination level setting circuit 52. If any of the level differences of the pairs of signals is greater than the allowable level difference as a result of the second comparison operation, the comparison circuit 53 outputs a defective signal indicating that the processed portion having the translucent property, which is processed on the sheet of paper W, as the object of inspection, is defective.

The correction circuit 58 adjusts the gains of the amplifier 56 in accordance with a rotating speed of the inspection cylinder 45. Specifically, even when the same amount of light is incident on the color camera 42, an output level of the CCD 42b becomes smaller as the rotating speed of the inspection cylinder 45 is faster. For this reason, an influence of the rotating speed is eliminated by the correction circuit 58. A phase signal of the inspection cylinder 45 is supplied to the memory controller 55, the comparison circuit 53, the correction circuit 58, and the CCD controller 59. A reference value memory signal is supplied to the memory controller 55. A determination start signal is supplied to the memory controller 55 and the comparison circuit 53.

The phase signal is originated from an output signal of a rotary encoder (not shown) configured to detect a rotational phase of the inspection cylinder 45. The phase signal includes a reference pulse which rises for each turn of the inspection cylinder 45, and a clock pulse which rises once at every predetermined number of turns of the inspection cylinder 45. The reference value memory signal is a signal used for causing the reference image data to be read into the reference memory 50 through the memory controller 55, and is supplied by an operation of a reference value memory switch (not shown) by an operator. The determination start signal is a signal instructing the start of the comparison operation between the reference image data and the detection image data, and is supplied by an operation of a determination start switch (not shown) by the operator.

In the above-described configuration, acquisition of the reference image data corresponding to the processed portion having the translucent property, which is processed on the sheet of paper W, takes place as a pre-process of a quality inspection step. First, the operator confirms a condition of the print on the sheet of paper W in the course of test printing using the sheet of paper W. When the condition of the print is confirmed to be fine, the supply of the reference value memory signal to the control device 46 is started by the operation of the reference value memory switch. Once a reference signal indicating a reference position of the inspection cylinder 45 is outputted from the rotary encoder, acquisition of the reference image data from the sheet of paper W held and conveyed by the inspection cylinder 45 is started, and the acquired data are stored in the reference memory 50.

After the reference image data on the sheet of paper W held and conveyed by the inspection cylinder 45 are stored in the reference memory 50, determination processing is started by supplying the determination start signal. In the determination processing, first of all, in response to the rotation of the inspection cylinder 95, detection image data on the sheet of paper W held and conveyed by the inspection cylinder 45 are read into the detection memory 51, as in the case of reading the reference image data. Next, the detection image data read in the determination processing are compared with the reference image data stored in advance. Then, appropriateness of the processed portion having the translucent property processed on the sheet of paper W is determined based on whether or not the level values of the two types of data fall within the corresponding allowable level difference.

For example, FIG. 3 shows an image taken with the color camera 42. Here, in each of numerous pieces (such as bank notes and securities) Wa on the sheet of paper W as the object of inspection, the ultraviolet rays emitted from the UV-LED illuminators 41a and 41b onto the imaging plane pass only through a processed portion PE having the translucent property processed on the sheet of paper W and hit the corresponding part of the luminescence-producing portion 45a of the inspection cylinder 45. Thus, the corresponding part of the luminescence-producing portion 45a produces the luminescence.

Then, the luminescence in the visible light range passes through the ultraviolet cut filter 43 (i.e., undergoes ultraviolet filtering) and is then made incident on the color camera 42. On the other hand, the remaining portion including a pattern portion VE printed with an ordinary visible ink reflects the ultraviolet rays directly. However, the reflected ultraviolet rays are eliminated by the ultraviolet cut filter 43 whereby the remaining portion appears darker.

As a consequence, it is possible to conduct detailed inspection of the presence, contour, and location of the processed portion PE having the translucent property such as a "watermark" or a "security window."

In this way, the inspection apparatus 40 according to the embodiment can inspect the processed portion PE having the translucent property and further enhance the printing quality of the sheet of paper W.

Needless to say, the present invention is not limited only to the foregoing embodiment and various changes are possible without departing from the gist of the present invention.

{Industrial Applicability}

The inspection apparatus for a sheet according to the present invention is applicable to a special printing press for printing bank notes, securities, and the like, where quality management is important.

{Reference Signs List}
40 Inspection Apparatus
41a, 41b UV-Led Illuminator (Light Source)
42 Color Camera (Imaging Means)
42a Lens
42b CCD (Charge Coupled Device)
43 Ultraviolet Cut Filter (Ultraviolet Filter)
44 Support Frame
45 Inspection Cylinder (Support Member)
45A Luminescence-Producing Portion
46 Control Device
50 Reference Memory
51 Detection Memory
52 Determination Level Setting Circuit
53 Comparison Circuit
55 Memory Controller
56 Amplifier
57 A/D Converter
58 Correction Circuit
59 CCD Controller
W Sheet of Paper (Sheet)
Wa Piece of Paper (Bank Note, Security, etc.)
PE Processed Portion Having Translucent Property
VE Pattern Portion Printed With Visible Ink

The invention claimed is:

1. An inspection apparatus for a sheet subjected to a process to impart a translucent property, comprising:
   a support member in which a surface facing the sheet is processed with a material to produce luminescence in a visible light range upon irradiation of ultraviolet rays;
   a light source configured to irradiate the sheet with light containing the ultraviolet rays;
   imaging means for imaging the sheet;
   an ultraviolet filter configured to eliminate the ultraviolet rays in the light emitted from the light source and reflected off the sheet and the support member, and to make only the light having wavelengths longer than wavelengths of the ultraviolet rays incident on the imaging means; and
   a control device configured to determine appropriateness of the process to impart a translucent property performed on the sheet on the basis of the luminescence in the visible light range produced by the support member and made incident on the imaging means.

* * * * *